(12) United States Patent
Cen et al.

(10) Patent No.: US 8,088,153 B2
(45) Date of Patent: Jan. 3, 2012

(54) MEDICAL EQUIPMENT FOR CORONARY ARTERY DISEASE

(76) Inventors: Liefang Cen, Guangzhou (CN); Zhiyong Cen, Guangdong (CN)

( * ) Notice: Subject to any disclaimer, the term of this patent is extended or adjusted under 35 U.S.C. 154(b) by 1103 days.

(21) Appl. No.: 11/508,250

(22) Filed: Aug. 23, 2006

(65) Prior Publication Data

US 2008/0051857 A1 Feb. 28, 2008

(51) Int. Cl.
*A61N 5/06* (2006.01)
(52) U.S. Cl. .............................................. 607/88; 606/1
(58) Field of Classification Search .............. 607/88–92; 606/1, 2, 8–12; 128/898
See application file for complete search history.

(56) References Cited

U.S. PATENT DOCUMENTS

| | | | |
|---|---|---|---|
| 5,374,283 A * | 12/1994 | Flick | 607/46 |
| 5,616,140 A * | 4/1997 | Prescott | 606/10 |
| 6,743,249 B1 * | 6/2004 | Alden | 607/88 |
| 6,860,896 B2 * | 3/2005 | Leber et al. | 607/1 |
| 2003/0009087 A1 * | 1/2003 | Keirsbilck | 600/300 |
| 2003/0109910 A1 * | 6/2003 | Lachenbruch et al. | 607/108 |
| 2006/0167532 A1 * | 7/2006 | Parker | 607/88 |
| 2007/0129776 A1 * | 6/2007 | Robins et al. | 607/88 |
| 2007/0288071 A1 * | 12/2007 | Rogers | 607/88 |

* cited by examiner

*Primary Examiner* — Ahmed M Farah

(57) ABSTRACT

The present invention relates to a low cost treatment device for coronary artery disease. The treatment device for coronary artery disease comprises a photonic glove, a heart-board, and a machine for controlling the photonic glove and the heart-board, which are electrically connected. The photonic glove includes 4 holes for the 4 fingers next to the thumb to wear, three fixed belts of the photon generating device, and at least one magic stick for fixing the belts of the photon generating device. One end of each fixed belt in the photon generating device is fixed to the front side of the photonic glove. Three photonic generators are assembled on the front side of the photonic glove, and the magic sticks are positioned on the back of the photonic glove. The present invention is low cost, friendly to use, and can work easily at home compared to the traditional invention.

4 Claims, 3 Drawing Sheets

MEDICAL EQUIPMENT FOR CORONARY ARTERY DISEASE

FIELD OF THE INVENTION

The present invention relates to a medical equipment. More particularly, it relates to a medical equipment for coronary artery disease.

BACKGROUND OF THE INVENTION

Cardiovascular disease (CVD) is the leading killer to human health. Currently the treatment of medicines for the disease is ineffective, a surgery treatment will be applied to patients when the disease gets worse, the medical fee for such treatment is difficultly accepted by the most people, also, after the treatment of Percutaneous Transluminal Coronary Angioplasty (PTCA), the incidence rate of recurrence still reach to 30~50% within 6 months, makes a crucial issue for the surgical treatment.

SUMMARY OF THE INVENTION

The present invention provides a medical equipment for coronary artery disease in low treatment cost.

The main object of the present invention is to provide a medical equipment for coronary artery disease, which comprises a photonic glove, a heart-board, and a machine unit for controlling the photonic glove and the heart-board. The three components are electrically connected. The photonic glove has 4 holes for 4 fingers to wear except the thumb in a hand, three fixing belts, and the self-stick reclosable fasteners for fastening the fixing belts. One end of each the fixing belt is fixed at the front side of the photonic glove, three photon generating devices are assembled on the fixing belts respectively, and the self-stick reclosable fasteners are positioned at the back of the photonic glove.

The present invention is low cost, user friendly, and can work easily at home compared with conventional arts.

DETAILED DESCRIPTION OF PRESENT INVENTION

Figure 1:
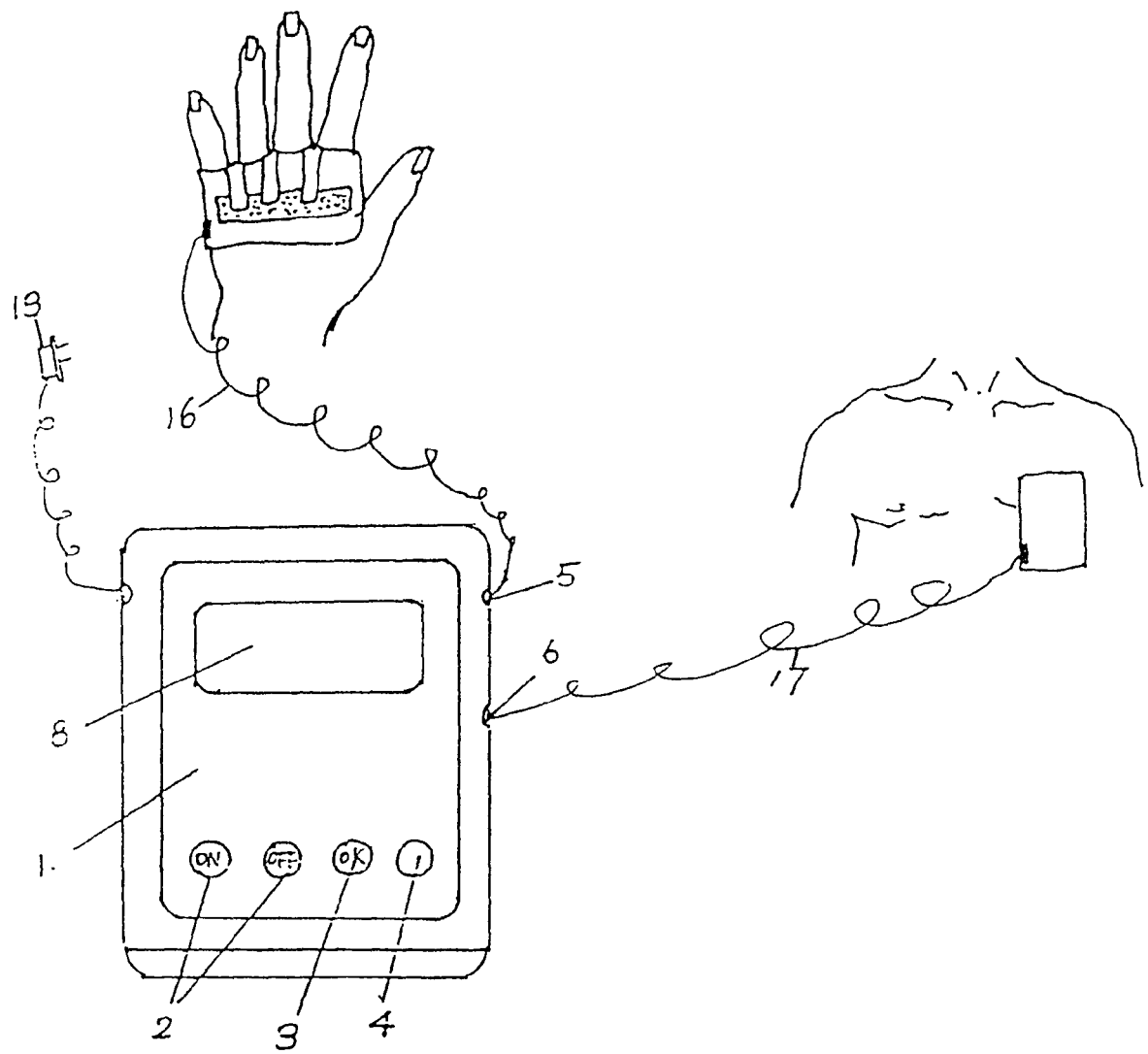
FIG. 1 is a schematic drawing showing the usage of present invention.
Figure 2:
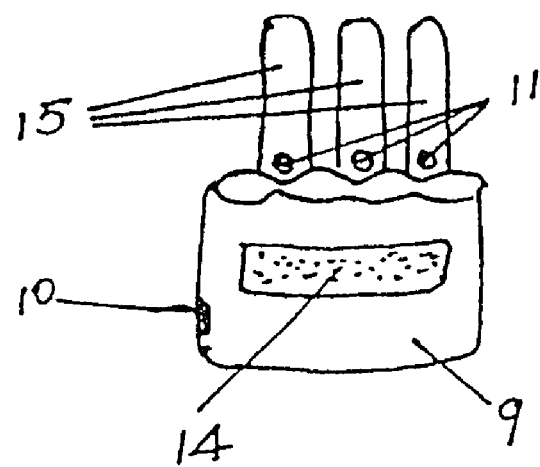
FIG. 2 is a schematic drawing showing the photonic glove of present invention.
Figure 3:
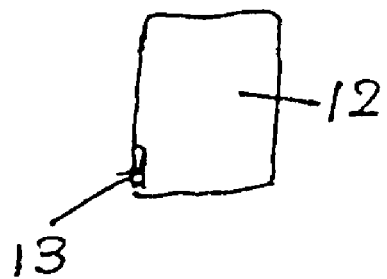
FIG. 3 is a schematic drawing showing the heart-board of present invention.
Figure 4:
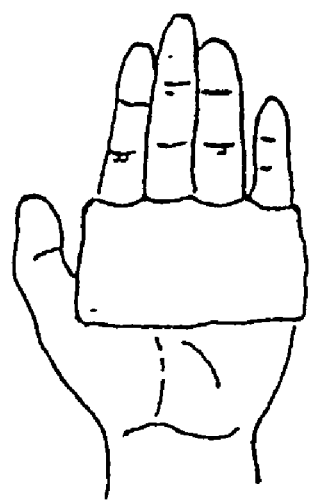
FIG. 4 and FIG. 5 are schematic drawings showing the photonic glove in use of present invention.
Figure 5:
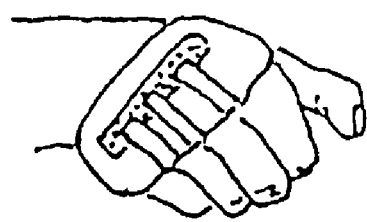

Please refer to FIGS. 1~3. The medical equipment for coronary artery disease comprises a machine unit 1, a photonic glove 9, a heart-board 12, and a charging rectifier 18. The photonic glove 9 and the heart-board 12 are electrically connected with the machine unit 1 through the photonic signal line 16 and the heart-board connecting line 17, respectively.

Machine unit 1 is used to control the photonic glove 9 and the heart-board 12. Inside the machine unit 1 includes a driving circuit, a photon power control circuit, a time control circuit, a charging circuit and a rechargeable battery. Additionally, on the panel of machine unit 1 includes a power switch 2, a confirmation key 3, an enable key of the heart-board 4, a photonic signal line socket 5, a heart-board connecting line socket 6 and a display 8.

Photonic glove 9 includes four holes for 4 fingers to wear except the thumb in a hand. One end of three fixing belts 15 is fixed at the front side of the photonic glove 9. Three photon generating devices 11 are assembled on the fixing belts respectively. The photonic glove 9 also includes a photonic signal line socket 10 and self-stick reclosable fasteners 14. The self-stick reclosable fasteners 14 are positioned at the back of the photonic glove 9 for fastening the fixing belts 15.

The heart-board 12 includes a heating line socket 13.

Please refer to FIGS. 1~5. Using the equipment of present invention, 4 fingers next to the thumb of a hand wear into the photonic glove 9. The fixing belts 15 are bended and fixed at the back of glove with the self-stick reclosable fasteners 14 through the gaps of fingers. Thus the photon generating devices 11 are separately positioned at the acupuncture points of the skin between fingers. Further, the photonic signal line 16 is plugged into the photonic signal line socket 5 of machine unit 1 and the photonic signal line socket 10 of the photonic glove 9. The heart-board connecting line 17 connects the heart-board connecting line socket 6 of machine unit 1 and the heart-board connecting 10 line socket 13 of the heart-board 12. By turning on the power switch 2 of machine unit 1 and press the confirmation key 3 and the enable key of the heart-board 4, the photon generating devices 11 will emit light on the acupuncture points of the skin, also the heart-board 12 will be heated and user need to put it touch closely to the body at the front area of the heart.

When machine unit 1 runs out the power, the charging rectifier 18 is plugged into the line power for charging.

What is claimed is:

1. A medical equipment for coronary artery disease, comprising:
    a photonic glove;
    a heart-board; and
    a machine unit for controlling said photonic glove and said heart-board,
    wherein said components are electrically connected to each other, wherein said photonic glove includes 4 holes for 4 fingers except thumb in a hand to wear, three fixing belts, and self-stick reclosable fastener for fastening the fixing belts, one end of each said fixing belt is fixed at the front side of the photonic glove, three photon generating devices are assembled on said fixing belts respectively, said the self-stick reclosable fastener is positioned at the back of the photonic glove.

2. A medical equipment for coronary artery disease according to claim 1, on the panel of said machine unit includes a power switch, a confirmation key, an enable key of the heart-board and a display.

3. A medical equipment for coronary artery disease according to claim 1, wherein said equipment also includes a photonic signal line and a heart-board connecting line, which connects said machine unit to said photonic glove and said heart-board respectively.

4. A medical equipment for coronary artery disease according to claim 1, wherein said machine unit also includes a photonic signal line socket and a heart-board connecting line socket, said photonic glove also includes a photonic signal line socket, said heart-board includes a heart-board connecting line socket, said photonic signal line connects to both said photonic signal line sockets on said machine unit and said photonic glove, and said heart-board connecting line connects to both said heart-board connecting line sockets on said machine unit and said heart-board.

* * * * *